US012696679B2

(12) United States Patent
Igarashi et al.

(10) Patent No.: US 12,696,679 B2
(45) Date of Patent: Jul. 28, 2026

(54) FULLERENE DERIVATIVE AND PRODUCTION METHOD THEREFOR

(71) Applicant: Resonac Corporation, Tokyo (JP)

(72) Inventors: Takeshi Igarashi, Kawasaki (JP); Chieko Nakagawa, Koriyama (JP)

(73) Assignee: MITSUBISHI CORPORATION, Tokyo (JP)

( * ) Notice: Subject to any disclaimer, the term of this patent is extended or adjusted under 35 U.S.C. 154(b) by 346 days.

(21) Appl. No.: 18/039,311

(22) PCT Filed: Dec. 6, 2021

(86) PCT No.: PCT/JP2021/044774

§ 371 (c)(1),
(2) Date: May 30, 2023

(87) PCT Pub. No.: WO2022/124273

PCT Pub. Date: Jun. 16, 2022

(65) Prior Publication Data

US 2024/0306486 A1 Sep. 12, 2024

(30) Foreign Application Priority Data

Dec. 9, 2020 (JP) ................................ 2020-204606

(51) Int. Cl.

| | |
|---|---|
| ***H10K 85/20*** | (2023.01) |
| ***C01B 32/156*** | (2017.01) |
| ***C07C 17/266*** | (2006.01) |
| ***C07C 22/08*** | (2006.01) |
| ***C07C 23/46*** | (2006.01) |
| ***C07D 307/93*** | (2006.01) |
| *H10K 30/30* | (2023.01) |

(52) U.S. Cl.

CPC ......... *H10K 85/215* (2023.02); *C01B 32/156* (2017.08); *C07C 17/266* (2013.01); *C07C 22/08* (2013.01); *C07C 23/46* (2013.01); *C07D 307/93* (2013.01); *C01P 2006/40* (2013.01); *C07C 2604/00* (2017.05); *H10K 30/30* (2023.02)

(58) Field of Classification Search

None

See application file for complete search history.

(56) References Cited

U.S. PATENT DOCUMENTS

| | | | |
|---|---|---|---|
| 5,382,719 | A | 1/1995 | Fagan |
| 2021/0376274 | A1 | 12/2021 | Furukawa et al. |

FOREIGN PATENT DOCUMENTS

| | | | |
|---|---|---|---|
| JP | 2013-140923 | A | 7/2013 |
| JP | 2016-178130 | A | 10/2016 |
| JP | 2019-099570 | A | 6/2019 |
| JP | 2019-142775 | A | 8/2019 |
| KR | 10-2020-0133762 | A | 11/2020 |
| WO | 2011/033973 | A1 | 3/2011 |
| WO | 2011/033974 | A1 | 3/2011 |
| WO | 2016/194630 | A1 | 12/2016 |
| WO | 2019/182143 | A1 | 9/2019 |

OTHER PUBLICATIONS

Korean Notice of Allowance dated Aug. 13, 2025 in Application No. 10-2023-7018924.

Brian J. Reeves et al., "Fluorous Fullerene Acceptors in Vacuum-Deposited Photovoltaic Cells", Solar RRL, 2019, 9 pages, 3, 1900070.

Semivrazhskaya et al., "Lower trifluoromethyl[70]fullerene derivatives: novel structural data and an survey of electronic properties", Electrochimica Acta, vol. 255, 2017, pp. 472-481.

Dorozhkin et al., "Synthesis, Structure, and Theoretical Study of Lower Trifluoromethyl Derivatives of [60]Fullerene", Eur. J. Org. Chem., 2007, pp. 5082-5094.

Communication issued Apr. 9, 2025 in Korean Application No. 10-2023-7018924.

*Primary Examiner* — Anthony Ho

(74) *Attorney, Agent, or Firm* — Sughrue Mion, PLLC

(57) ABSTRACT

A fullerene derivative having a partial structure shown in the following General Formula (1) is provided.

[Chem. 1]

(1)

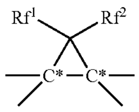

(in Formula (1), C*'s are adjacent carbon atoms that form a fullerene framework. $Rf^1$ and $Rf^2$ each independently represents a perfluoroalkyl group having 1 to 4 carbon atoms, and $Rf^1$ and $Rf^2$ may be linked to each other to form a ring structure).

15 Claims, 3 Drawing Sheets

・・・(C1a)

・・・(C1b)

・・・(C2)

・・・(C3)

・・・(C4)

・・・(C5)

・・・(C6)

・・・(C7)

FULLERENE DERIVATIVE AND PRODUCTION METHOD THEREFOR

CROSS REFERENCE TO RELATED APPLICATIONS

This application is a National Stage of International Application No. PCT/JP2021/044774 filed on Dec. 6, 2021, claiming priority based on Japanese Patent Application No. 2020-204606 filed on Dec. 9, 2020.

TECHNICAL FIELD

The present invention relates to a fullerene derivative, a thin film, a photoelectric conversion element, a solid-state imaging device and a method for producing a fullerene derivative.

Priority is claimed on Japanese Patent Application No. 2020-204606, filed Dec. 9, 2020, the content of which is incorporated herein by reference.

BACKGROUND ART

Fullerenes are composed of carbon molecules with a closed-shell structure, and are used in various fields due to their stable structure, improved light absorption properties and favorable electrical properties. In addition, in recent years, various fullerene derivatives in which substituents are bonded to fullerenes have been developed. On the other hand, photoelectric conversion elements are elements that convert light into an electrical signal using a photoelectric effect, and include photodiodes, optical transistors and the like, and can be applied to electronic devices such as solid-state imaging devices. Therefore, in the development of photoelectric conversion elements, techniques using fullerenes having improved light absorption properties and favorable electrical properties or derivatives thereof have been focused on, and the development of such elements has become important. For example, Patent Document 2 discloses a photoelectric conversion element.

Patent Document 1 discloses a fullerene derivative exhibiting sublimability and having a plurality of branched alkyl chains.

Non-Patent Document 1 describes fullerene derivatives (60-2-1, etc.) having a plurality of trifluoromethyl groups. In addition, Non-Patent Document 1 also describes a fullerene derivative ($C_{60}CF_2$) having a difluoromethano structure.

CITATION LIST

Patent Document

[Patent Document 1]

Japanese Unexamined Patent Application, First Publication No. 2019-99570

[Patent Document 2]

PCT International Publication No. WO2016/194630

Non-Patent Document

[Non-Patent Document 1]

Brian J. Reeves et al., Solar RRL 2019, 3, 1900070.

SUMMARY OF INVENTION

Technical Problem

Fullerene derivatives may have a structure in which a fused ring of a pentagonal ring and an aromatic ring is substituted with a substituent, thus increasing steric hindrance and reducing the number of pi-conjugated systems compared to unsubstituted fullerenes. Therefore, fullerene derivatives can reduce aggregation of fullerenes during vapor deposition and improve film formation properties compared to unsubstituted fullerenes, and can effectively reduce modification of optical properties such as modification of an absorption wavelength range that may occur due to aggregation.

However, many fullerene derivatives have a problem in that they are thermally decomposed when heated during vapor deposition. In addition, fullerene derivatives exhibiting sublimability also have problems in that the sublimation temperature is too high and synthesis is difficult.

For example, the fullerene derivative listed in the synthesis example of Patent Document 1 has a relatively high sublimation temperature of 400° C. or higher, which is close to the decomposition temperature of this derivative, making stable vapor deposition difficult.

Although the fullerene derivative having a trifluoromethyl group described in Non-Patent Document 1 has a low sublimation temperature of lower than 400° C., it is not suitable for mass production because a special reaction device is required for synthesis.

In addition, the fullerene derivative having a difluoromethano structure described in Non-Patent Document 1 has a high sublimation temperature and is not practical.

The present invention has been made in view of the above circumstances, and an object of the present invention is to provide a fullerene derivative that can be synthesized without requiring a special synthesis device and can be vapor-deposited at a low temperature without being thermally decomposed. In addition, another object of the present invention is to provide a photoelectric element including the fullerene derivative and an image sensor including the photoelectric element.

Solution to Problem

In order to achieve the above objects, the present invention provides the following aspects.

A first aspect of the present invention provides the following fullerene derivative.

[1]

A fullerene derivative including a fullerene framework, and a partial structure represented by the following General Formula (1):

[Chem. 1]

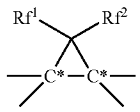

(1)

(in Formula (1), C*'s are adjacent carbon atoms that form the fullerene framework, $Rf^1$ and $Rf^2$ each independently represents a perfluoroalkyl group having 1 to 4 carbon atoms, and $Rf^1$ and $Rf^2$ may be linked to each other to form a ring structure).

The fullerene derivative according to the first aspect of the present invention preferably has the following features. Combinations of two or more of the following features are preferable.

[2] The fullerene derivative according to [1], wherein the fullerene framework is composed of $C_{60}$, $C_{70}$, $C_{74}$, $C_{76}$, or $C_{78}$.

[3] The fullerene derivative according to [1] or [2], wherein $Rf^1$ and $Rf^2$ are a trifluoromethyl group.

[4] The fullerene derivative according to any one of [1] to [3], wherein one fullerene framework includes one partial structure represented by Formula (1).

[5] A thin film including the fullerene derivative according to any one of [1] to [4].

A second aspect of the present invention provides the following photoelectric conversion element.

[6] A photoelectric conversion element, including:

a first electrode and a second electrode that face each other; and an organic layer disposed between the two electrodes, wherein the organic layer contains the fullerene derivative according to any one of [1] to [4].

A third aspect of the present invention provides the following solid-state imaging device.

[7] A solid-state imaging device comprising the photoelectric conversion element according to [6].

A fourth aspect of the present invention provides the following method for producing a fullerene derivative.

[8] A method for producing the fullerene derivative according to any one of [1] to [4], including a process of reacting a fullerene and a compound represented by the following Formula (2) in the presence of a base:

[Chem. 2]

(2)

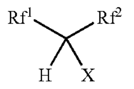

(in Formula (2), X represents a halogen atom, and $Rf^1$ and $Rf^2$ are the same as those in Formula (1)).

Advantageous Effects of Invention

The fullerene derivative of the present invention can be synthesized without using a special reaction device, also sublimates at a low temperature without being thermally decomposed, and thus is useful as a fullerene derivative used for film formation according to a vapor deposition method.

BRIEF DESCRIPTION OF THE DRAWINGS

FIG. 1 shows the chemical formula of Compound 1a.

DESCRIPTION OF EMBODIMENTS

Figure 1:
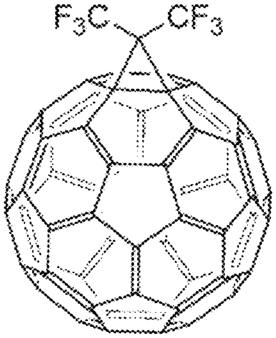

Hereinafter, the configurations of preferable embodiments of the present invention will be described. The present invention can be appropriately modified and implemented as long as the gist thereof is not changed. Numbers, materials, amounts, shapes, numerical values, ratios, positions, configurations and the like can be changed, added, omitted, substituted, and combined without departing from the scope of the present invention.

[Fullerene Derivative]

A fullerene derivative of the present embodiment is a compound having a partial structure represented by Formula (1) in a fullerene framework. In the present embodiment, "fullerene derivative" refers to a compound having a structure in which a specific group is added to these fullerene frameworks, and "fullerene framework" refers to a carbon framework constituting a closed-shell structure derived from a fullerene.

[Chem. 3]

(1)

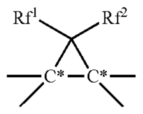

(in Formula (1), C*'s are adjacent carbon atoms that form a fullerene framework, $Rf^1$ and $Rf^2$ each independently represents a perfluoroalkyl group having 1 to 4 carbon atoms, and $Rf^1$ and $Rf^2$ may be linked to each other to form a ring structure).

In addition, the fullerene derivative of the present embodiment has the structure of Formula (1) in which a perfluoro group is bonded to a fullerene framework via a methano group. Therefore, it has a property of a low sublimation temperature, and can be suitably used for film formation according to vapor deposition.

$Rf^1$ and $Rf^2$ each represents a perfluoroalkyl group, and each has 1 to 4 carbon atoms. The number of carbon atoms may be, for example, 1 to 2 or 3 to 4. The numbers of carbon atoms for $Rf^1$ and $Rf^2$ may be the same as or different from each other. If the number of carbon atoms is more than 4, the obtained fullerene derivative may melt during heating and may not sublimate. In addition, when $Rf^1$ and $Rf^2$ are linked to each other to form a ring structure, the formed ring structure is a 3- to 9-membered ring, and preferably a 5- to 7-membered ring. For example, as necessary, it may be a 4- to 8-membered ring or a 6- to 7-membered ring.

Specific examples of $Rf^1$ and $Rf^2$ include a trifluoromethyl group, pentafluoroethyl group, heptafluoropropyl group, heptafluoroisopropyl group, nonafluorobutyl group, nonafluoroisobutyl group, nonafluoro-sec-butyl group, and nonafluoro-tert-butyl group. A trifluoromethyl group is particularly preferable in consideration of case of availability of raw materials. In addition, specific examples of cases in which $Rf^1$ and $Rf^2$ are linked to each other to form a ring structure include an octafluorobutylene group, decafluoropentene group, and dodecafluorohexene group.

The fullerene framework in the fullerene derivative of the present embodiment can be arbitrarily selected, and a fullerene framework having 60 to 200 carbon atoms is preferable. The number of carbon atoms may be, as necessary, 60 to 150, 60 to 100, 60 to 90, 60 to 80, or 60 to 70. Specific examples of fullerene frameworks include $C_{60}$, $C_{70}$, $C_{76}$, $C_{78}$, $C_{82}$, $C_{84}$, $C_{90}$, $C_{94}$, $C_{96}$, $C_{120}$, and $C_{200}$, and among these, $C_{60}$, $C_{70}$, $C_{74}$, $C_{76}$ or $C_{78}$ is more preferable, $C_{60}$ or $C_{70}$ is still more preferable, and $C_{60}$ is particularly preferable. This is because raw material fullerenes tend to have a higher purity when the number of carbon atoms is smaller, with Coo tending to have a particularly higher purity than other fullerenes.

When the fullerene derivative of the present embodiment has the above structure, the sublimation temperature can be lowered. Therefore, the fullerene derivative can be vapor-deposited by sublimation without being decomposed. The number of partial structures represented by Formula (1) with respect to one fullerene framework is preferably plural because in this case it is possible to lower the sublimation temperature, and on the other hand, it is preferably 1 because the complexity of synthesis and purification is avoided. The number of partial structures represented by Formula (1) may be, as necessary, for example, 1 to 50, 1 to 30, 1 to 20, 1 to 10, 1 to 5, 1 to 3, 1 to 2, or only 1.

Whether vapor deposition through sublimation is possible can be confirmed simply through thermogravimetric analysis. In thermogravimetric analysis, if a temperature at which a weight loss of 10% relative to the initial weight occurs is 400° C. or lower under a nitrogen atmosphere, vapor deposition is generally possible, and if the temperature at which a weight loss of 50% relative to the initial weight occurs is 400° C. or lower, vapor deposition can be more reliably performed. The lower limit of these temperatures can be arbitrarily selected, and may be, for example, 200° C. or higher, but the present invention is not limited thereto. The temperature at which a 10% weight loss occurs may be, for example, 400° C. or lower, 380° C. or lower, 360° C. or lower, 340° C. or lower, 320° C. or lower, 300° C. or lower, or 280° C. or lower. The temperature at which a weight loss of 50% relative to the initial weight occurs may be, for example, 400° C. or lower, 380° C. or lower, 360° C. or lower, 340° C. or lower, 320° C. or lower, 300° C. or lower, or 280° C. or lower. The temperature at which a 10% weight loss occurs is lower than the temperature at which a 50% weight loss occurs. The difference between these temperatures can be arbitrarily selected, and may be, for example, 45 to 65° C., 40 to 60° C., or 35 to 55° C.

[Method for Producing a Fullerene Derivative]

The method for producing a fullerene derivative of the present embodiment is not particularly limited, and for example, the following method may be exemplified. That is, the fullerene and the compound represented by Formula (2) are reacted in the presence of a base to obtain the fullerene derivative represented by Formula (1).

[Chem. 4]

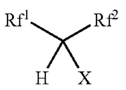

(2)

(in Formula (2), X represents a halogen atom, and $Rf^1$ and $Rf^2$ are the same as those in Formula (1))

The fullerene used for the reaction can be arbitrarily selected, and one having 60 to 200 carbon atoms is preferable. The number of carbon atoms may be, as necessary, 60 to 150, 60 to 100, 60 to 90, 60 to 80, or 60 to 70. Specific examples of fullerenes include $C_{60}$, $C_{70}$, $C_{76}$, $C_{78}$, $C_{82}$, $C_{84}$, $C_{90}$, $C_{94}$, $C_{96}$, $C_{120}$, and $C_{200}$, and among these, $C_{60}$, $C_{70}$, $C_{74}$, $C_{76}$ or $C_{78}$ is more preferable, $C_{60}$ or $C_{70}$ is still more preferable, and $C_{60}$ is particularly preferable.

In Formula (2), X represents a halogen atom, and examples of halogen atoms include chlorine, bromine, and iodine, and in consideration of the reactivity, X is preferably iodine. Preferable examples of $Rf^1$ and $Rf^2$ are the same as those in Formula (1).

In addition, a solvent may be used for this reaction, and is not particularly limited, and one that dissolves the fullerene and the compound of Formula (2) is preferable. For example, benzene, toluene, xylene, trimethylbenzene, chlorobenzene, and 1,2-dichlorobenzene may be exemplified. Among these, 1,2-dichlorobenzene is preferable because the fullerene and the compound of Formula (2) have high solubility therein.

The base is not particularly limited, and examples thereof include metal hydroxides such as sodium hydroxide and potassium hydroxide, metal carbonates such as sodium carbonate, potassium carbonate, and cesium carbonate, metal alkoxides such as sodium ethoxide, potassium ethoxide, and potassium-tert-butoxide, and organic bases such as pyridine, triethylamine, and diazabicycloundecene, and among these, potassium-tert-butoxide is preferable in consideration of its excellent reaction yield. The bases may be used alone or two or more thereof may be used in combination. The amount of the base can be arbitrarily selected, and examples thereof include 0.01 to 100 molar equivalents with respect to the compound represented by Formula (2).

In addition, a phase-transfer catalyst may be used in order to increase the solubility of the base in the solvent or increase the reaction rate. Examples of phase transfer catalysts include crown ethers such as 18-crown-6-ether and 15-crown-5-ether and polyalkylene glycols such as polyethylene glycol dimethyl ether. Crown ethers are preferable and 15-crown-5-ether is particularly preferable because it greatly increases the reaction rate. The phase transfer catalysts may be used alone or two or more thereof may be used in combination. The amount of the base can be arbitrarily selected, and examples thereof include 0.01 to 500 molar equivalents with respect to the compound represented by Formula (2).

When the reaction temperature for this reaction is higher, the reaction easily progresses, and when the reaction temperature is lower, the reaction selectivity is higher and the yield of a desired product is improved. From this viewpoint, the reaction temperature may be selected depending on the purpose. Generally, it is preferable to select a temperature between −50° C. and the boiling point of the solvent used, and it is more preferable to select a temperature between −20° C. and 50° C. For example, the reaction temperature for this reaction may be, as necessary, −50° C. to −20° C., −20° C. to −5° C., −5° C. to 0° C., 0° C. to 10° C., 10° C. to 30° C., or 30° C. to 50° C., as examples.

Regarding the reaction time for this reaction, it is preferable to perform the reaction for a long time until the reaction sufficiently progresses in order to obtain a high yield. In order to increase the production amount, it is preferable to complete one reaction in a short time and repeat such a reaction a plurality of times before the reaction rate slows down. From this viewpoint, the reaction time is selected depending on the purpose, and generally, it is preferable to select a time between 1 minute and 120 hours, it is more preferable to select a time between 5 minutes and 24 hours, and it is still more preferable to select a time between 30 minutes and 12 hours.

The pressure during the reaction is not particularly limited, and pressurization may or may not be performed. For example, when it is desirable that the reaction occur at a temperature close to or equal to higher than the boiling point of the solvent, the reaction can be performed under pressure. When pressurizing, the pressure can be preferably selected, for example, between atmospheric pressure and 10 atm. The reaction is preferably performed at atmospheric pressure so that a special device such as a pressurization instrument is unnecessary and costs can be kept low.

The order of mixing a fullerene, a compound represented by Formula (2), a base, and a solvent can be arbitrarily selected. For example, the fullerene may be dissolved in the solvent, and the compound represented by Formula (2) and the base may be then additionally added and mixed. However, the present invention is not limited to this example.

[Thin Film]

The thin film of the present embodiment contains a fullerene derivative. The thin film may be formed by any method such as a wet film formation method such as spin coating or slit coating or a dry film formation method such as vapor deposition, and is preferably formed by vapor deposition.

The thin film may be composed of only the fullerene derivative of the present embodiment or may be composed of a mixture of other compounds.

The thin film of the present embodiment tends to maintain the intrinsic properties of the fullerene derivative without damaging the chemical bonds thereof. Accordingly, compared to a thin film of unsubstituted fullerenes (for example, $C_{60}$), which tend to aggregate during film formation, optical properties can be improved, and additionally, it is possible to improve the properties of a photoelectric conversion element and a solid-state imaging device described below.

The light absorption properties of the thin film containing the fullerene derivative of the present embodiment are different to those of a thin film containing unsubstituted fullerenes. In the thin film containing the fullerene derivative of the present embodiment, abnormal light absorption in a short wavelength visible light range of 400 nm to 500 nm is reduced. Abnormal light absorption is considered to be caused by aggregation of fullerenes or fullerene derivatives. For example, the absorption coefficient of the thin film containing the fullerene derivative of the present embodiment at a wavelength of 450 nm is smaller than the absorption coefficient of a thin film containing unsubstituted fullerenes at a wavelength of 450 nm. For example, the absorption coefficient of a thin film containing a fullerene derivative at a wavelength of 450 nm is ½ or less than the absorption coefficient of a thin film containing unsubstituted fullerenes at a wavelength of 450 nm.

[Photoelectric Conversion Element]

The photoelectric conversion element of the present embodiment includes a first electrode and a second electrode that face each other and an organic layer disposed between the two electrodes. The organic layer contains the fullerene derivative represented by Formula (1). In addition, the organic layer may contain compounds other than the fullerene derivative. The first electrode and the second electrode are not particularly limited, and known materials and the like can be used.

In addition, the structure of the photoelectric conversion element of the present embodiment is not particularly limited as long as the photoelectric conversion element has the above properties. Examples of structures of the photoelectric conversion element include the structure described in Patent Document 2.

[Solid-State Imaging Device]

The solid-state imaging device (image sensor) of the present embodiment includes one or more photoelectric conversion elements. In addition, although the solid-state imaging device can be applied to various electronic devices, and can be preferably applied to, for example, mobile phones and digital cameras, the present invention is not limited thereto.

While preferable embodiments of the present invention have been described in detail above, the present invention is not limited to the specific embodiments, and various modifications or changes can be made within the spirit and scope of the present invention described in the claims.

EXAMPLES

Hereinafter, the present invention will be described in detail with reference to examples. The present invention is not limited to these examples.

(Synthesis Example 1) Synthesis of Compound 1a and Compound 1b

Figure 2:
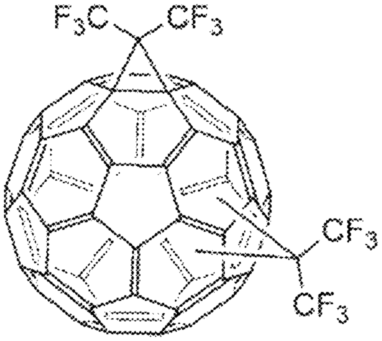
FIG. 2 shows the chemical formula of Compound 1b.

In a 50 mL eggplant flask, $C_{60}$ (216 mg, 0.3 mmol) was dissolved in 1,2-dichlorobenzene (20 mL) and cooled in an ice bath. Potassium-tert-butoxide (67 mg, 0.6 mmol), 1,1,1,3,3,3-hexafluoro-2-iodopropane (92 mg, 0.33 mmol), and 15-crown-5-ether (264 mg, 1.2 mmol) were added thereto, and the mixture was then stirred while cooling in an ice bath and reacted for 6 hours. The reaction was performed at atmospheric pressure. After the reaction, the reaction mixture was purified by preparative HPLC (column: COSMOSIL PBB commercially available from Nacalai Tesque, Inc. (an inner diameter of 20 mm, a length of 250 mm), eluent: toluene), and a fraction containing Compound 1a and a fraction containing Compound 1b were obtained. This solvent was distilled off, the obtained solid was washed with methanol and dried, and 84 mg of Compound 1a and 40 mg of Compound 1b were obtained as a dark brown solid. The chemical formula of Compound 1a is shown in FIG. 1 as (C1a), and the chemical formula of Compound 1b is shown in Drawings in FIG. 2 as (C1b). Compound 1b is a mixture of isomers with different substituent positions.

(Synthesis Example 2) Synthesis of Compound 2

Figure 3:
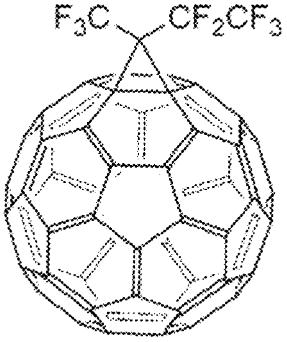
FIG. 3 shows the chemical formula of Compound 2.

Synthesis was performed in the same manner as in Synthesis Example 1 except that the same molar amount of 1,1,1,3,3,4,4,4-octafluoro-2-iodobutane was used in place of 1,1,1,3,3,3-hexafluoro-2-iodopropane, and 79 mg of Compound 2 was obtained as a dark brown solid. The chemical formula of Compound 2 is shown in FIG. 3 as (C2).

(Synthesis Example 3) Synthesis of Compound 3

Figure 4:
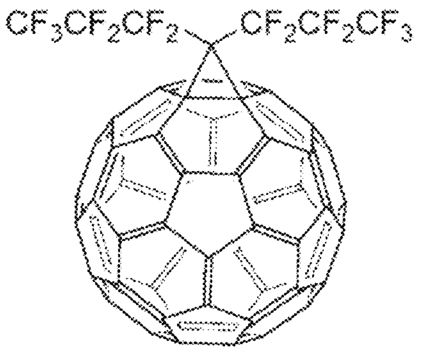
FIG. 4 shows the chemical formula of Compound 3.

Synthesis was performed in the same manner as in Synthesis Example 1 except that the same molar amount of 1,1,1,2,2,3,3,5,5,6,6,7,7,7-tetradecafluoro-4-iodoheptane was used in place of 1,1,1,3,3,3-hexafluoro-2-iodopropane, and 91 mg of Compound 3 was obtained as a dark brown solid. The chemical formula of Compound 3 is shown in FIG. 4 as (C3).

(Synthesis Example 4) Synthesis of Compound 4

Figure 5:
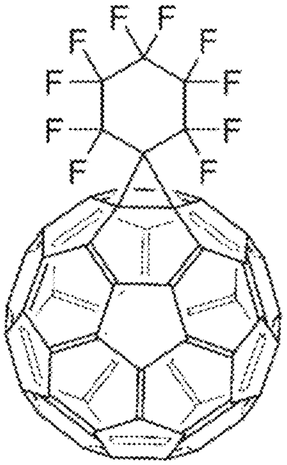
FIG. 5 shows the chemical formula of Compound 4.

Synthesis was performed in the same manner as in Synthesis Example 1 except that the same molar amount of 2,2,3,3,4,4,5,5,6,6-decafluoro-1-iodocyclohexane was used in place of 1,1,1,3,3,3-hexafluoro-2-iodopropane, and 80 mg of Compound 4 was obtained as a dark brown solid. The chemical formula of Compound 4 is shown in FIG. 5 as (C4).

(Synthesis Example 5) Synthesis of Compound 5

Figure 6:
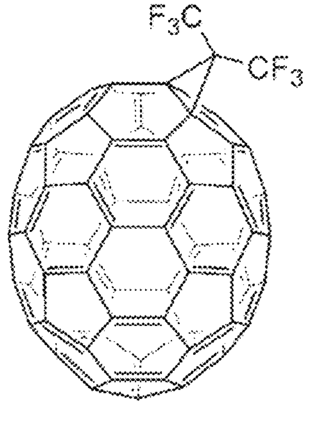
FIG. 6 shows the chemical formula of Compound 5.

Synthesis was performed in the same manner as in Synthesis Example 1 except that the same molar amount of $C_{70}$ was used in place of $C_{60}$, and 68 mg of Compound 5 was obtained as a dark brown solid. The chemical formula of Compound 5 is shown in FIG. 6 as (C5).

(Synthesis Example 6) Synthesis of Compound 6

Figure 7:
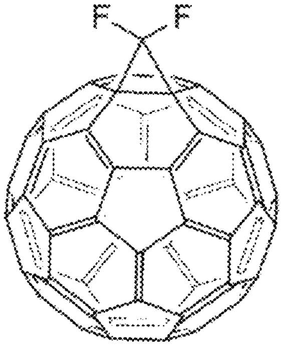
FIG. 7 shows the chemical formula of Compound 6.

Compound 6 (C6) was obtained by the method described in Non-Patent Document 1. The chemical formula of Compound 6 is shown in FIG. 7 as (C6).

(Synthesis Example 7) Synthesis of Compound 7

Figure 8:
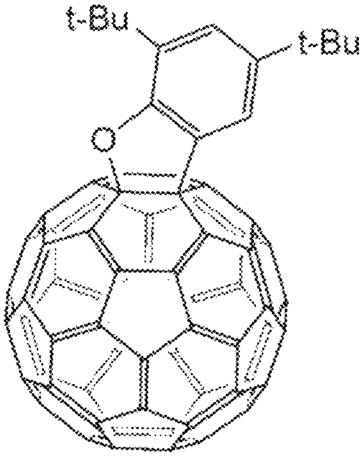
FIG. 8 shows the chemical formula of Compound 7.

Compound 7 (C7) was obtained by the method of Synthesis Example 1 in Patent Document 1. The chemical formula of Compound 7 is shown in FIG. 8 as (C7).

Example 1-1

Thermogravimetric analysis of Compound 1a in a vacuum was performed in order to check whether vapor deposition through sublimation of Compound 1a was possible and check the sublimation temperature. A sample (about 5 mg) was set in a vacuum thermogravimetric analysis device (VPE-9000 commercially available from Advance Riko., Inc.). The temperature was raised from room temperature to 1,000° C. at a rate of 10° C./min in a vacuum of 1 Pa or less. The temperature at which the weight of the sample had decreased by 10% from the initial weight was defined as Ts (° C.) (−10%), and the temperature at which the weight of the sample had decreased by 50% was defined as Ts (° C.) (−50%). The results are shown in Table 1.

Examples 1-2 to 1-6 and Comparative Examples 1-1 to 1-4

Thermogravimetric analysis was performed in the same manner as in Example 1 except that compounds shown in Table 1 were used in place of Compound 1a. The results are shown in Table 1.

TABLE 1

| | Compound | Ts (° C.) (−10%) | Ts (° C.) (−50%) |
|---|---|---|---|
| Example 1-1 | Compound 1a | 350 | 390 |
| Example 1-2 | Compound 1b | 300 | 350 |
| Example 1-3 | Compound 2 | 330 | 380 |
| Example 1-4 | Compound 3 | 320 | 380 |
| Example 1-5 | Compound 4 | 360 | 400 |
| Comparative Example 1-1 | Fullerene $C_{60}$ | 450 | 500 |
| Comparative Example 1-2 | Compound 6 | 640 | 690 |
| Comparative Example 1-3 | Compound 7 | 400 | 450 |
| Example 1-6 | Compound 5 | 420 | 460 |
| Comparative Example 1-4 | Fullerene $C_{70}$ | 510 | 560 |

Comparing Examples 1-1 to 5 having a $C_{60}$ fullerene framework with Comparative Example 1-1, it can be seen that the fullerene derivative of the present invention could be sublimated at a temperature lower than that of the unsubstituted fullerene ($C_{60}$) of Comparative Example 1-1. In addition, comparing Example 1-6 having a $C_{70}$ fullerene framework with Comparative Example 1-4, the same tendency was observed even when the fullerene framework was $C_{70}$.

In addition, comparing Examples 1-1 to 5 with Comparative Examples 1-2 to 3, the fullerene derivative of the present invention could be sublimated at a temperature lower than that of fullerene derivatives conventionally known to sublimate.

Example 2-1

Compound 1a was vapor-deposited on a glass substrate, and light absorption properties of the vapor-deposited thin film were evaluated. A thin film was produced by performing vapor deposition on a dry glass substrate washed with isopropyl alcohol (IPA) and acetone using an ultrasonic cleaning device at a rate of 0.1 to 1.0 Å/s under a high vacuum. The light absorption properties were evaluated using a UV-Vis spectrophotometer (UV-2400 commercially available from Shimadzu Corporation) at an absorption coefficient of 450 nm. The results are shown in Table 2.

Examples 2-2 to 2-6 and Comparative Examples 2-1 to 2-2

Light absorption properties were evaluated in the same manner as in Example 2-1 except that compounds shown in Table 2 were used in place of Compound 1a. The results are shown in Table 2.

TABLE 2

| | Compound | Absorption coefficient ($10^5$ $cm^{-1}$) |
|---|---|---|
| Example 2-1 | Compound 1a | 0.27 |
| Example 2-2 | Compound 1b | 0.26 |
| Example 2-3 | Compound 2 | 0.28 |
| Example 2-4 | Compound 3 | 0.30 |
| Example 2-5 | Compound 4 | 0.25 |
| Comparative Example 2-1 | Fullerene $C_{60}$ | 0.55 |
| Example 2-6 | Compound 5 | 0.53 |
| Comparative Example 2-2 | Fullerene $C_{70}$ | 0.97 |

Table 2 shows that the thin films containing fullerene derivatives having a $C_{60}$ fullerene framework of the present invention (Examples 2-1 to 2-5) had a smaller absorption coefficient at 450 nm than the thin film containing the unsubstituted fullerene $C_{60}$ (Comparative Example 2-1). In addition, the thin film containing the fullerene derivative having a $C_{70}$ fullerene framework of the present invention (Example 2-6) had a smaller absorption coefficient at 450 nm than the thin film containing the unsubstituted fullerene $C_{70}$ (Comparative Example 2-2). As a result, it was confirmed that the fullerene derivative of the present invention did not exhibit abnormal light absorption properties in a visible light short wavelength range due to aggregation.

INDUSTRIAL APPLICABILITY

A fullerene derivative is provided that can be synthesized without requiring a special synthesis device and can be vapor-deposited at a low temperature without being thermally decomposed.

The fullerene derivative of the present invention can be preferably used for photoelectric elements, solid-state imaging devices and the like.

The invention claimed is:

1. A fullerene derivative including a fullerene framework, and a partial structure represented by the following General Formula (1):

[Chem. 1]

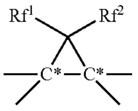

(1)

(in Formula (1), C*'s are adjacent carbon atoms that form the fullerene framework, $Rf^1$ and $Rf^2$ each independently represents a perfluoroalkyl group having 1 to 4 carbon atoms, and $Rf^1$ and $Rf^2$ may be linked to each other to form a ring structure), wherein $Rf^1$ and $Rf^2$ are a trifluoromethyl group.

2. The fullerene derivative according to claim 1, wherein the fullerene framework is composed of $C_{60}$, $C_{70}$, $C_{74}$, $C_{76}$, or $C_{78}$.

3. The fullerene derivative according to claim 1, wherein one fullerene framework includes one partial structure represented by Formula (1).

4. A thin film comprising the fullerene derivative according to claim 1.

5. A photoelectric conversion element, comprising:

a first electrode and a second electrode that face each other; and an organic layer disposed between the two electrodes, wherein the organic layer contains the fullerene derivative according to claim 1.

6. A solid-state imaging device comprising the photoelectric conversion element according to claim 5.

7. A method for producing the fullerene derivative according to claim 1, including a process of reacting a fullerene and a compound represented by the following Formula (2) in the presence of a base:

[Chem. 2]

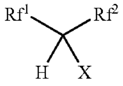

(2)

(in Formula (2), X represents a halogen atom, and $Rf^1$ and $Rf^2$ are the same as those in Formula (1)).

8. The method for producing a fullerene derivative according to claim 7, wherein the base is at least one selected from the group consisting of a metal hydroxide, a metal carbonate, a metal alkoxide, pyridine, triethylamine, and diazabicycloundecene.

9. The method for producing a fullerene derivative according to claim 8, wherein the base is at least one selected from the group consisting of sodium hydroxide, potassium hydroxide, sodium carbonate, potassium carbonate, cesium carbonate, sodium ethoxide, potassium ethoxide, potassium-tert-butoxide, pyridine, triethylamine, and diazabicycloundecene.

10. The method for producing a fullerene derivative according to claim 7, wherein X is iodine.

11. The method for producing a fullerene derivative according to claim 7, wherein the fullerene is $C_{60}$, $C_{70}$, $C_{74}$, $C_{76}$, or $C_{78}$.

12. The method for producing a fullerene derivative according to claim 7, wherein a phase-transfer catalyst is used in the process of reacting the fullerene and the compound represented by Formula (2).

13. The method for producing a fullerene derivative according to claim 12, wherein the phase-transfer catalyst is at least one selected from the group consisting of 18-crown-6-ether, 15-crown-5-ether, and polyethylene glycol dimethyl ether.

14. The method for producing a fullerene derivative according to claim 7, wherein the process of reacting the fullerene and the compound represented by Formula (2) is performed at a temperature of −50° C. to 50° C.

15. The method for producing a fullerene derivative according to claim 7, further including a process of mixing the fullerene and a solvent before the process of reacting the fullerene and the compound represented by Formula (2).

* * * * *